United States Patent
Srinivasan

(10) Patent No.: US 10,543,141 B2
(45) Date of Patent: Jan. 28, 2020

(54) ISOLETTE ENVIRONMENT CONTROLLER AND METHOD

(71) Applicant: Advanced Imaging Research, Inc., Cleveland, OH (US)

(72) Inventor: Ravi Srinivasan, Beachwood, OH (US)

(73) Assignee: ADVANCED IMAGING RESEARCH, INC., Cleveland, OH (US)

( * ) Notice: Subject to any disclaimer, the term of this patent is extended or adjusted under 35 U.S.C. 154(b) by 207 days.

(21) Appl. No.: 15/560,333

(22) PCT Filed: Mar. 23, 2015

(86) PCT No.: PCT/US2015/021939
§ 371 (c)(1),
(2) Date: Sep. 21, 2017

(87) PCT Pub. No.: WO2016/153472
PCT Pub. Date: Sep. 29, 2016

(65) Prior Publication Data
US 2018/0064595 A1 Mar. 8, 2018

(51) Int. Cl.
*A61G 11/00* (2006.01)
*A61B 5/055* (2006.01)

(52) U.S. Cl.
CPC ......... *A61G 11/006* (2013.01); *A61B 5/0555* (2013.01); *A61G 11/009* (2013.01); *A61G 2203/20* (2013.01); *A61G 2203/46* (2013.01); *A61G 2210/90* (2013.01)

(58) Field of Classification Search
CPC ...... A61G 11/00; A61G 11/006; A61F 7/0053
USPC ...................................... 600/21–22
See application file for complete search history.

(56) References Cited

FOREIGN PATENT DOCUMENTS

| GB | 2346560 1 | 8/2000 |
|----|-----------|--------|
| WO | WO 2013/165263 A1 | 11/2013 |

OTHER PUBLICATIONS

International Search Report and Written Opinion for International Application No. PCT/US2015/021939, dated Dec. 7, 2015.

*Primary Examiner* — John P Lacyk
(74) *Attorney, Agent, or Firm* — Kusner & Jaffe

(57) ABSTRACT

An apparatus and method of controlling a temperature within an isolette includes obtaining a temperature of ambient air external to the isolette, obtaining a base-line ambient air temperature, and calculating a maximum heater power level based on a relationship between the base-line ambient air temperature and the actual ambient air temperature.

18 Claims, 6 Drawing Sheets

ISOLETTE ENVIRONMENT CONTROLLER AND METHOD

RELATED APPLICATION DATA

This application is a National Stage of international application no. PCT/US2015/021939, filed on Mar. 23, 2017 is incorporated herein by reference in its entirety.

TECHNICAL FIELD

The present disclosure relates to isolettes for providing a microenvironment for an infant and, more particularly, to an apparatus and method for regulating the microenvironment in an isolette.

BACKGROUND OF THE INVENTION

Infants who need special care are placed in a specialized area, such as a neonatal intensive care unit (NICU), pediatric infant care unit (PICU), cardiac intensive care unit (cICU), etc. within a hospital. Pre-term and term sick newborns that demand a special environment are kept in a warm isolette (at higher temperatures up to 39 deg C.). These delicate newborns demand special care and therefore are generally left in the NICU and are not transported to other hospital sections, including sections for non-invasive imaging-based diagnostic procedures. Thus diagnosis and follow-up patient care is limited to moderately ill infants and is not generally extended to severely ill infants.

Magnetic resonance (MR) imaging is a safe, non-ionizing radiation-based diagnostic imaging tool that is routinely used in the characterization of illnesses of the brain, heart or major organs in the torso (liver, kidney, spleen, pelvis etc.). Diagnosis/prognosis of patients depends on the MR image quality. Patient, user and equipment safety and equipment performance cannot be compromised. Each diagnostic procedure must be carried out in its fullest without being restricted by the equipment.

Additional risks are associated when fragile infants are disturbed, let alone transported outside of their clinical sections. Nevertheless, the benefits of diagnosis outweigh these risks.

An isolette for tomographic examination according to Koch et al. (U.S. Pat. No. 5,800,335 issued Sep. 1, 1998) was of a modular design, but the isolette failed to encompass the entire sub system. Heater switching circuitry used in the isolette produced artifacts during MR scanning. Further, during imaging the isolette is placed inside a RF coil, which compromised image quality as the isolette produced artifacts in the image.

The concept of an RF coil inside the isolette was introduced by Nordell et al. (see International Publication Number WO98/48756 A1, published Nov. 5, 1998). A receive only RF coil was introduced inside the isolette for effective scanning. Fluid flow turbines or related technology was used to propel air needed to achieve even temperatures inside the isolette volume. A stand-alone monitor was used in a base unit situated near the MR patient table to display vital signs of the patient. Signal lines normally stretched from the MR patient table where the patient was placed to the base unit located at the foot of the MR patient table. The unit worked as proposed but the "stretched" lines hampered efficient performance from time to time as they obstructed the patient and thus made it difficult to attend to the patient. For example, when immediate access to the patient was sought one had to carefully juggle his/her way through the lines inside the room.

A solution to this problem was addressed by Rohling et al. (U.S. Pat. No. 6,611,702 issued Aug. 26, 2003) where the entire isolette and the monitoring unit were built on to a GE MRI patient table. The unit was bulky to haul around the hospital, and it took a minimum of three people to maneuver the unit from the NICU to the MR section. The isolette was not modular and thus the entire unit was transported, which limited access to certain sections of the hospital. The RF coil disclosed in Rohling et al. encompassed the entire newborn, the filling factor was low and as a result low signal-to-noise ratios (SNRs) were realized despite the radial extended birdcage RF coil design. The same holds true for Feenan et al. (U.S. Pat. No. 7,599,728 issued Oct. 9, 2009) which was a combination of a neonate incubator with a neonate sized magnetic resonance imaging system. However, the detector RF coil was located outside the neonate incubator and thus image SNR was compromised.

With a magnetic resonance imaging (MRI) compatible transport isolette (Lonnekker et al., U.S. Pat. No. 7,278,962 issued Oct. 9, 2007), patient transfers and hence diagnostic studies are possible. However, the single structural design in which all components are incorporated within the unit resulted in a very long isolette (e.g., over six feet long). The unit was very bulky, weighed roughly ninety-five pounds and was cumbersome to transfer between the trolley and the MRI patient table.

Further, the isolette had an internal motor, and when inserted into the magnet this motor was relatively close to the magnet. As a result, slight lapping with the main magnet bore could cause interaction with the main magnet, with time varying gradients and/or with radiofrequency from the whole body transmit coil. The motor also limited incubator travel on the MRI table and hence infant diagnostic imaging studies. Additionally, close proximity of electronics to the MRI created a source for direct and indirect (from other equipment in the scan room) MRI artifacts in the low signal to noise images, which may be seen as noise bands and can obscure diagnosis.

While temperature regulation in the isolette of Lonnekker was somewhat attained based on feedback from air sensors near patient compartments, the isolette did not adjust to the changing environment, e.g., when being transferred from a relatively warm NICU to a relatively cold MRI scan room. More particularly, patient travel starts in the ICU which is kept warm and thus the equipment is pre-warmed and as a result the isolette quickly attains equilibrium. When the isolette is transferred to MRI scanner, which is significantly cooler than the hospital clinical section (ICU etc.), the isolette, despite its double walled enclosure, has to work harder to reach equilibrium but due to the cooler environment the process is significantly slower. When the unit is returned back to the ICU the opposite occurs. More particularly, due to the transition from the cold environment to the warm environment the unit may reach excessive temperatures and may overheat. Patient skin temperature can be used for thermoregulation and can somewhat assist the regulation process but does not account for environment change and air flow outside the isolette, as commonly encountered in all MRI scanners which are configured to cool patients and the body coil. Elevated temperatures can accelerate brain injury whereas lower temperatures can lead to hypothermia and water loss, both of which are deleterious to the patient.

Additionally, close proximity of the isolette fan to the patient section (aggregate section) introduced excessive audio noise which was not desired by the user or suitable to the patient. Further, a display screen of the isolette may not be viewed if the MRI observation window was not in-line with the MRI magnet bore. Moreover, nearly continuous MR exams on different patients were not possible with this design, as it has to be disinfected between studies delaying the process therefore rendering it inefficient for routine hospital use.

Recently a number of applications from Rapoport regarding neonate closed life support system (US2012/0071745 published Mar. 22, 2012 and US 2013/0267765 published Oct. 10, 2013), life support environment chamber (US 2013/0109956 published May 2, 2013), neonate cradle (US 2014/0039295 published Feb. 6, 2014) and neonate incubator and MRI docking station (US 2014/0128725 published May 8, 2014) have been disclosed. All of Rapoport's applications have one theme in common, to not disconnect the patient from life sustaining and monitoring lines available in the NICU. But efforts to counteract the MRI problems with these lines and monitoring equipment traditionally used in the unit were not discussed, leading to potential confusion as to the operation of the system. Generally, equipment found in the clinical unit are not MRI compatible and thus require re-connecting the patient to MRI compatible accessories or lengthening the existing lines such that the non MRI compatible components are away from the MRI magnet. The smaller the magnet, the smaller the problems and lower the risks (albeit still existent), see Feenan's *728 application for a self-contained incubator system and neonatal MRI combination as well as "Imaging the preterm infant: practical issues by Elia F Maalouf and Serena J Counsell in Part 1, Chapter 2, of book MRI of the Neonatal Brain by Dr. Mary Rutherford, London, Saunders, 2001) which describes a neonatal MRI sized magnet and a cradle (FIG. 2.1 therein).

Recently an MRI compatible infant imaging sub system by Srinivasan (U.S. Pat. No. 8,147,396 issued Apr. 3, 2012) allowed transfer of patients between intensive care and radiology sections where the patient was left undisturbed during inter-section transport including the MRI exam. Improvements to the radio-frequency (RF) coil design for high signal to noise ratio (SNR) and to fit inside this isolette were made by Srinivasan (U.S. Pat. No. 6,992,486 issued Jan. 31, 2006). In addition, compatibility of Lonneker's isolette to MR was described by Srinivasan (see U.S Patent Publication Number 20040116799 published Jun. 17, 2004]), which describes a novel environment adaptable isolette in the best interest of the patient, user and hospital safety.

SUMMARY OF THE INVENTION

An apparatus and method in accordance with the present disclosure enable the environment within an isolette to be precisely controlled, even when the isolette is subjected to sudden environmental changes due to movement from one location to another. The apparatus and method in accordance with the present disclosure adapt to ambient conditions to provide precise temperature control within the isolette without compromising patient care or safety. Further, the isolette in accordance with the present disclosure is virtually free in its placement location relative to the MRI apparatus, thereby permitting unlimited imaging, and enhancing patient, user and equipment safety.

According to one aspect of the invention, a method of controlling a temperature within an isolette is provided, where the isolette includes a patient section for housing an infant and for receiving heated air from a heater. The method includes: obtaining a temperature of ambient air external to the isolette; obtaining a base-line ambient air temperature; calculating a maximum heater power level based on a relationship between the base-line ambient air temperature and the actual ambient air temperature.

In one embodiment, calculating a maximum heater power includes using a ratio of the base-line ambient temperature relative to the actual ambient temperature.

In one embodiment, calculating includes calculating the maximum heater power using the formula $Hp=Tb/Ta*Pr$, where $Hp$ is the calculated maximum heater power, $Tb$ is the base-line ambient temperature, $Ta$ is the actual ambient temperature, and $Pr$ is the regulated power of the heater.

In one embodiment, the method includes: obtaining a temperature setpoint for the patient section; obtaining an actual temperature of the patient section; and regulating the actual temperature of the patient section by controlling the heater based on a relationship between the patient section temperature setpoint and the patient section actual temperature.

In one embodiment, regulating the actual temperature includes using a PID controller to control an amount of heat supplied by the heater.

In one embodiment, obtaining an actual temperature of the patient section includes: using a first temperature sensor to obtain a first temperature of the patient section; using a second temperature sensor to obtain a second temperature of the patient section; and removing power from the heater when a deviation between the first temperature and the second temperature exceeds a prescribed value.

In one embodiment, the method includes generating a warning when the deviation between the first temperature and the second temperature exceeds the prescribed value.

According to another aspect of the invention, an isolette includes: a patient section for housing an infant; a heater for providing heat to the patient section; and a controller operatively coupled to the heater, the controller including logic configured to obtain a temperature of ambient air external to the isolette; logic configured to obtain a base-line ambient air temperature; logic configured to calculate a maximum heater power level based on a relationship between the base-line ambient air temperature and the actual ambient air temperature.

In one embodiment, the logic configured to calculate a maximum heater power includes logic configured to use a ratio of the base-line ambient temperature relative to the actual ambient temperature to perform the calculation.

In one embodiment, the logic configured to calculate includes logic configured to calculate the maximum heater power using the formula $Hp=Tb/Ta*Pr$, where $Hp$ is the calculated maximum heater power, $Tb$ is the base-line ambient temperature, $Ta$ is the actual ambient temperature, and $Pr$ is the regulated power of the heater.

In one embodiment, the isolette includes: logic configured to obtain a temperature setpoint for the patient section; logic configured to obtain an actual temperature of the patient section; and logic configured to regulate the actual temperature of the patient section by controlling the heater based on a relationship between the patient section temperature setpoint and the patient section actual temperature.

In one embodiment, the logic configured to regulate the actual temperature includes logic configured to use a PID controller to control an amount of heat supplied by the heater.

In one embodiment, the logic configured to obtain an actual temperature of the patient section includes: logic configured to use a first temperature sensor to obtain a first temperature of the patient section; logic configured to use a second temperature sensor to obtain a second temperature of the patient section; and logic configured to remove power from the heater when a deviation between the first temperature and the second temperature exceeds a prescribed value.

In one embodiment, the isolette includes logic configured to generate a warning when the deviation between the first temperature and the second temperature exceeds the prescribed value.

According to another aspect of the invention, a controller for regulating a temperature within a patient section of an isolette includes: a processor and memory; and logic stored in the memory and executable by the processor, wherein when executed by the processor the logic causes the processor to perform the method described herein.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

In the annexed drawings, like references indicate like parts or features.

DEFINITIONS

Figure 1:
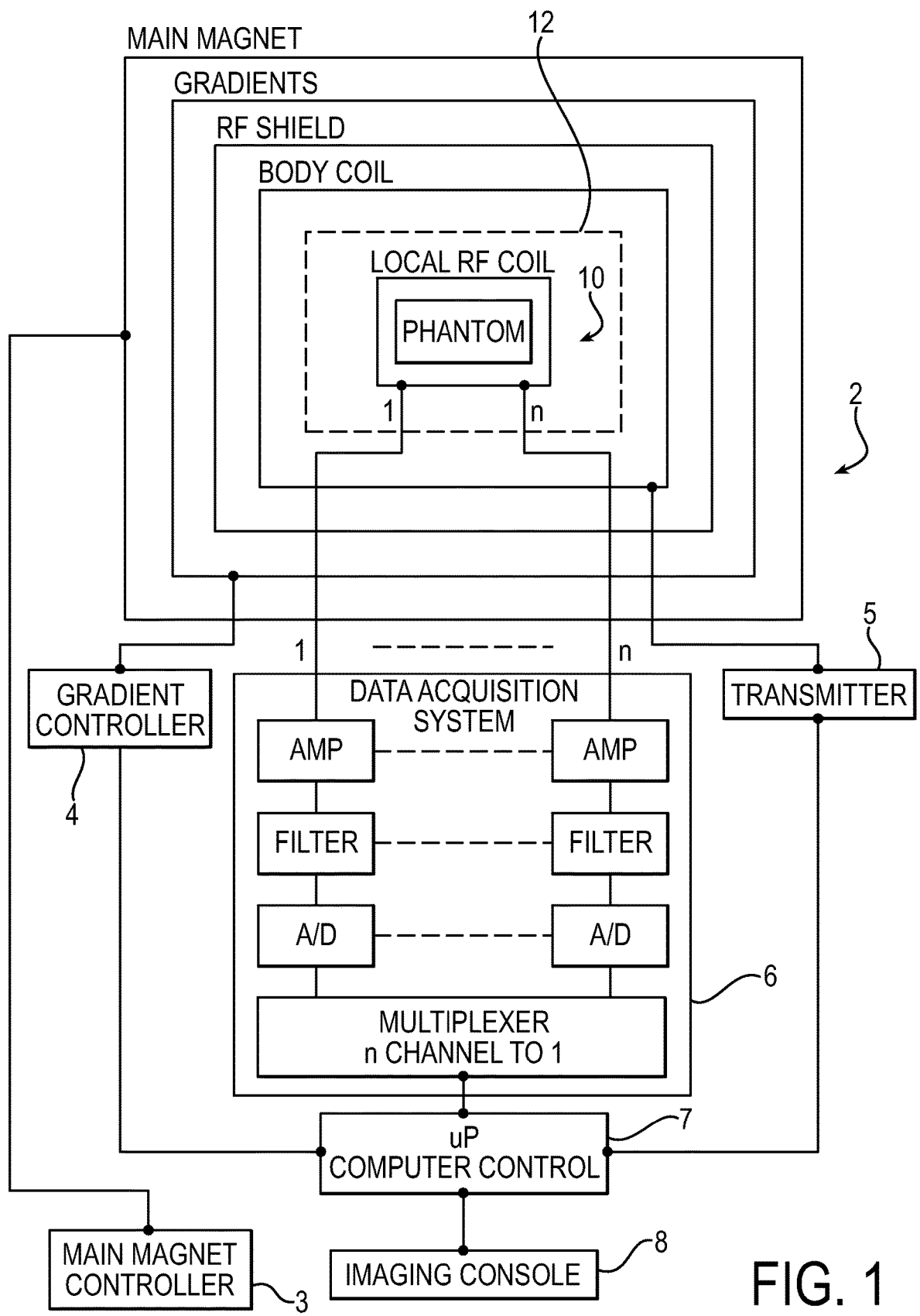
FIG. 1 is a block diagram of an exemplary MR system.

The term "infant" (Latin word infans, meaning unable to speak or speechless) relates to a newborn baby, premature baby or otherwise small baby generally from birth up to one year in age.

The term "radiology procedure" relates to non-invasive, resonance and non-resonance based imaging tools used for diagnosis and prognosis of illnesses.

The term "magnetic resonance" relates to techniques associated with anatomy, morphology, blood flow, biochemical properties, etc., including imaging, angiography, spectroscopy of the water proton and other metabolites such as phosphorous, sodium, lithium, etc. exhibiting magnetic resonance property.

The term "transport" relates to safely moving an infant along with life sustaining equipment and monitoring tools.

The term "modular system" relates to a system in which individual components can be quickly assembled and disassembled for ease of installation, de-installation, service, trouble shooting, design constraints, usability, etc.

The term "sub-system" relates generally to a subset of the infant isolette imaging system, mainly the infant isolette imaging system without the main diagnostic imaging equipment.

DESCRIPTION

A modular infant imaging sub-system design in accordance with the present disclosure facilitates ease of service and aids in final assembly and design (e.g., it facilitates different configurations, such as different alternating current (AC 100-240 VAC, 50/60 Hz) power supplies, etc.). The infant imaging sub system in accordance with the present disclosure may include a power system that can be powered by standard AC power (e.g., via a wall outlet) or via DC power (e.g., via a battery backup power supply available on a trolley). The power system can include a transformer to provide maximum patient isolation to high voltages and leakage currents. The sub-system includes an isolette that can be easily removed from a trolley by simply unplugging an electrical cable connector, thereby enabling immediate replacement of the isolette with an already sterile isolette. This rapid isolette swap on/off the trolley permits back-to-back infant imaging studies to be performed without MRI down time, thereby maximizing MRI efficiency.

Rapid introduction and removal of MRI compatible RF coils via a rear door superior to the infant allows seamless, perturbation free operation for carrying out unlimited safe diagnosis of the infant. Further, a single ended air supply can be used to minimize the chance of cross-contamination between patients. Fresh air can be drawn in from the ambient environment, for example, from behind a motor 62 through a dust filter followed by a micro-particle clinical filter. The air can be drawn through an air channel where it is warmed and humidified via guides on either side of an isolette patient section (e.g., along the entire length of the isolette), and the warmed and humidified air can be bled away to the isolette surrounding environment via portals (e.g., portals used for passing patient life sustaining and monitoring lines to the respective equipment and for routing cables for interfacing coils to the MRI). Filtered air can be continuously pushed throughout the isolette and over the infant to eliminate chances of cross-contamination between infants. Filtered air also helps minimize carbon-dioxide ($CO_2$) build up inside the patient section (note larger amounts of $CO_2$ can be deleterious to the subject).

A remotely located motor can propel freshly filtered air directionally over a heater and virtually eliminate motor driven audio noise in the patient chamber. For example, a low audible noise technology fan design can be used, which can result in audio noise within the patient chamber being less than 50 dbA. Close proximity of the heater to the patient section can provide increased system efficiency, although a remote heater design can be utilized as well. Filtered air can be forced over the heater and inside air channels, which minimize heat loss to environment. Careful adjustment of the channels can balance air flow and temperature inside the patient section within limits well below international performance standards (International Electrotechnical Commission IEC 60601-2-20). Sensor dependent, independent feedback and redundancy can be used in one or more locations throughout the isolette to improve performance, safety and effectiveness. Software and hardware measures can be incorporated to minimize risk while enhancing patient, operator and equipment safety.

Referring to FIG. 1, a block diagram of an MR system 2 that can be used in conjunction with an imaging sub-system in accordance with the present disclosure is shown. The MR system 2 includes a main magnet controller 3, a gradient controller 4, a transmitter 5 and a data acquisition system 6, as is conventional. A computer controller 7 controls the operation of the system, and system data is provided to a user through an imaging console 8. A local radiofrequency (RF) coil 10 of a neonate imaging sub-system 12 sends and receives data to/from the data acquisition system 6.

Figure 2:
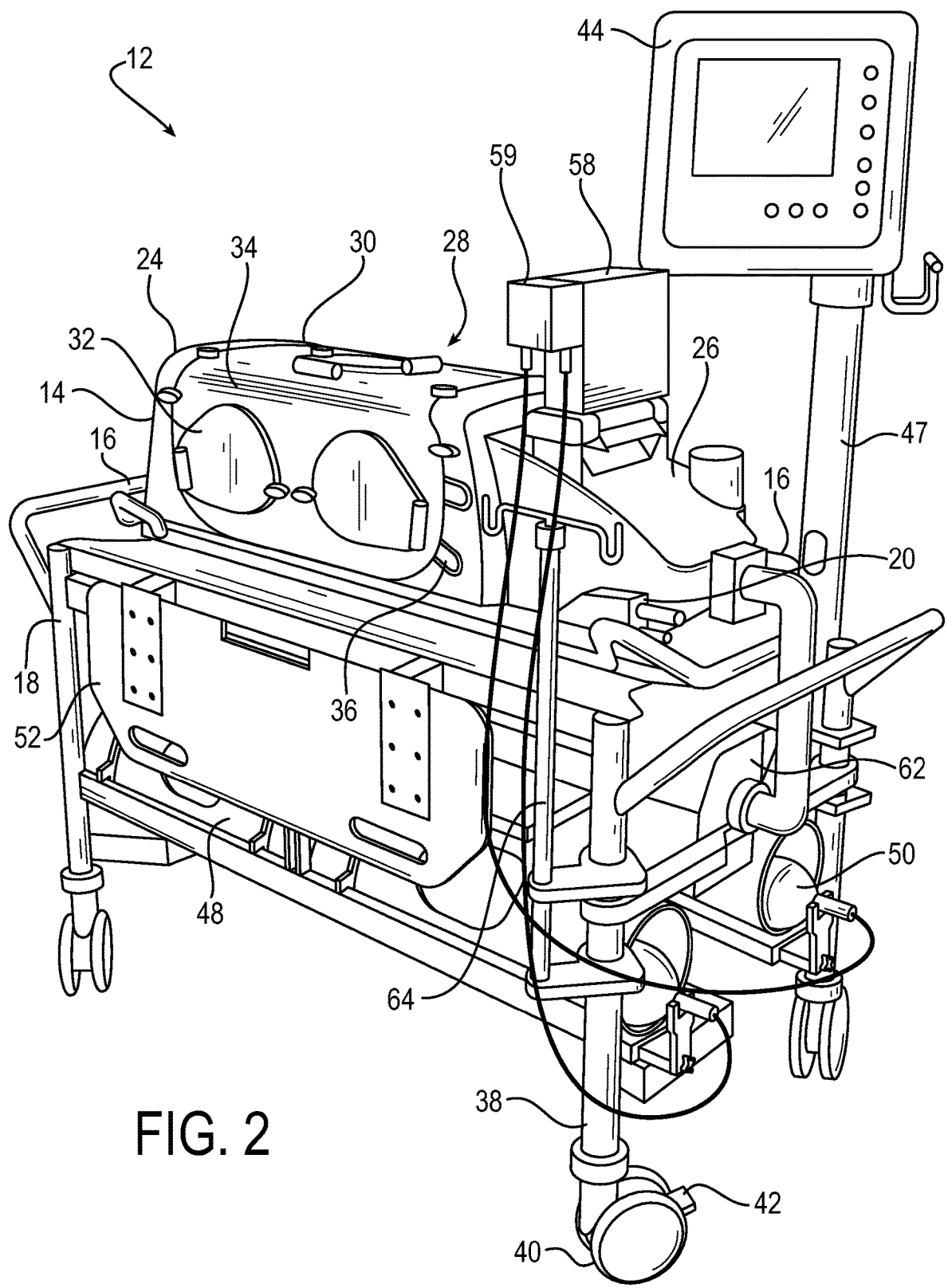
FIG. 2 illustrates an exemplary imaging sub-system including an isolette in accordance with the present disclosure.

Referring now to FIG. 2, an MR compatible neonate imaging sub-system 12 in accordance with an embodiment of the present disclosure is shown. The sub-system 12 includes various components, such as life sustaining equipment, vital signs monitoring equipment, and controlled environment equipment. Additionally, the imaging sub-system 12 can be modular, which facilitates removal and/or installation of various sub-components. For example, additional or different vital signs monitoring equipment can be easily added to and/or removed from the sub-system via quick release couplings. Generally, such modular components are coupled to the sub-system using hand operable locking clasps, for example. It is contemplated, however, that in some instances it may be preferable to use a relatively more secure coupling means, such as threaded fasteners or the like, to couple a component to the sub-system. Furthermore, the modularity of the sub-system facilitates transporting the sub-system to various locations. If a component is not required, it easily can be removed, thus reducing the weight and size of the sub-system.

The entire sub-system 12 is MR compatible, which permits safe and effective radiographic examination of the subject without affecting the isolette performance or the image quality. Moreover, the infant can remain in the isolette during the transport to and from the MR scan room as well as during the MR scan. This facilitates the well-being of the infant, as his/her micro environment is not disturbed. Additionally, life sustaining and monitoring lines can remain coupled to the infant at all times, even during MR scanning.

Throughout this disclosure reference will be made to MR compatible components, e.g., an MR compatible monitor or an MR compatible ventilator. Details on fabricating and/or modifying such components for compatibility with MR are provided in U.S. patent application Ser. No. 10/723,325 filed Nov. 26, 2003 and titled IMPROVED COMPATIBILITY OF ACCESSORY OF MAGNETIC RESONANCE, which is incorporated by reference herein. Accordingly, details regarding preparation of a component or components for MR compatibility will not be discussed in detail herein.

Briefly, interference with static magnetic fields can be reduced or eliminated by using non-interference generating components, such as non-magnetic components and/or non-conductive, non-metallic plastic components. These types of components do not produce a water signal, have very little or no ground leakage electrical currents (below 500 microamperes), and very little or no eddy currents. Thus, artifacts due to the components can be reduced and/or eliminated. For example, circulating currents within the components that can come in contact with the subject can be eliminated through the use of non-conductive materials, which are intended to enhance patient safety.

Additionally, the components should be transparent to the main magnetic field of the MR system 2. Metal components should be non-magnetic (e.g., strontium, phosphor-bronze, beryllium-copper, copper, aluminum, silver, gold etc.) and preferably have a low permeability, e.g., a permeability that will cause less than 1 percent eddy currents, ghosting and/or distortion of the image in all three axis X, Y, Z, respectively, particularly in low signal to noise scans with echo times less than 2.0 milliseconds. In most cases, diamagnetic and ferromagnetic materials should be limited, and in some cases diamagnetic and ferro-magnetic materials should not be used.

Interference due to time varying gradient magnetic fields can be reduced using intermediate frequency (IF) filters. For example, IF filters and feed-thru capacitors can be placed in all signal lines (e.g., data carrying lines), wherein the feed-thru capacitors either block all of the interferences or shunt them to ground. Additionally, gradient interferences can be minimized by reducing the size of the metals used in shielding the isolette electronics or by keeping them away from the gradient field of view (FOV). Ghosting or aliasing can be minimized by eliminating moving metal parts and by placing the metal sections away from the gradient crossovers along the magnet axis.

RF interference can be minimized by appropriate filtering mechanisms in passive signal lines and the active lines (lines that carry power). RF chokes can be used to prevent RF leakage, whereas high power RF filters capable of carrying a few amperes with very high impedances can be utilized.

Infant Isolette

Figure 3:
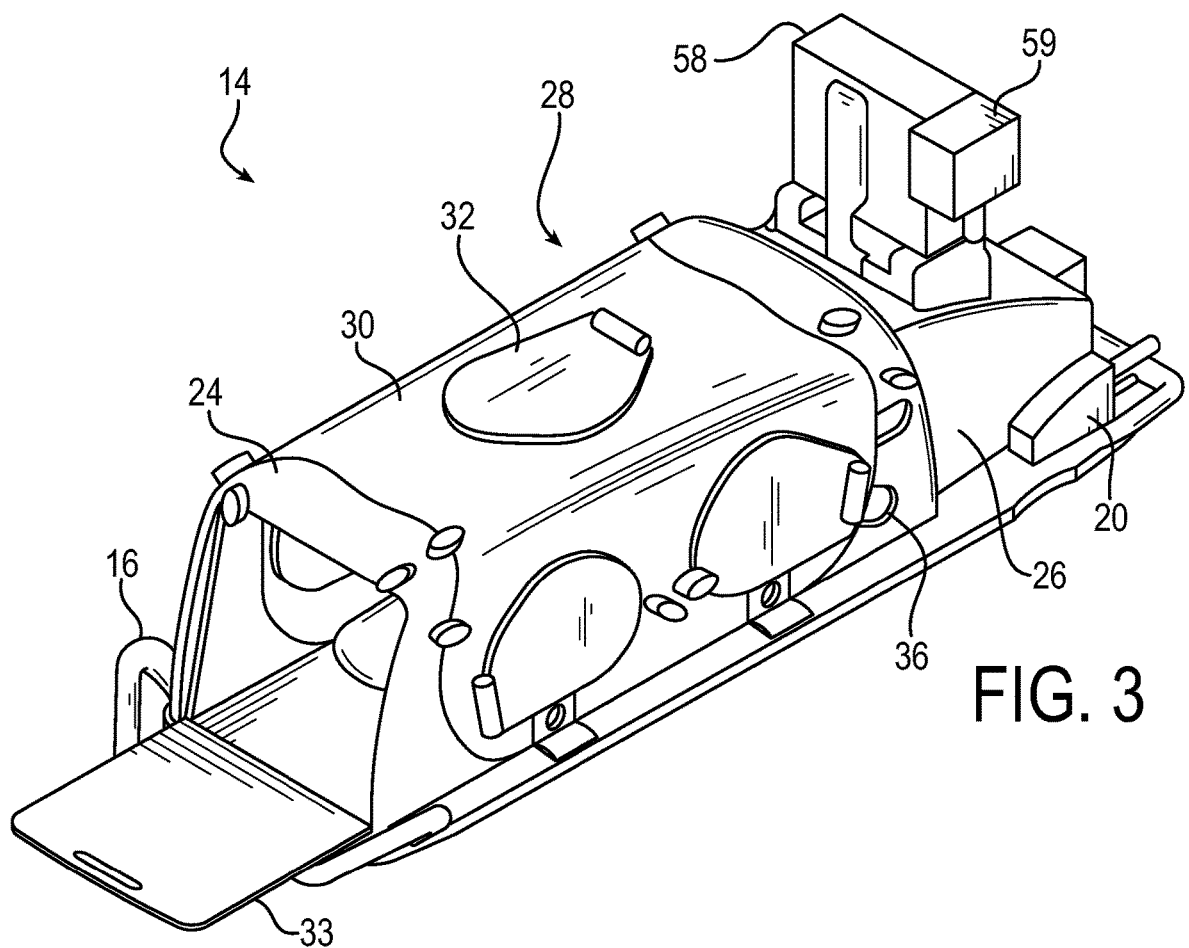
FIG. 3 is a perspective view of an exemplary modular isolette in accordance with the present disclosure.
Figure 4:
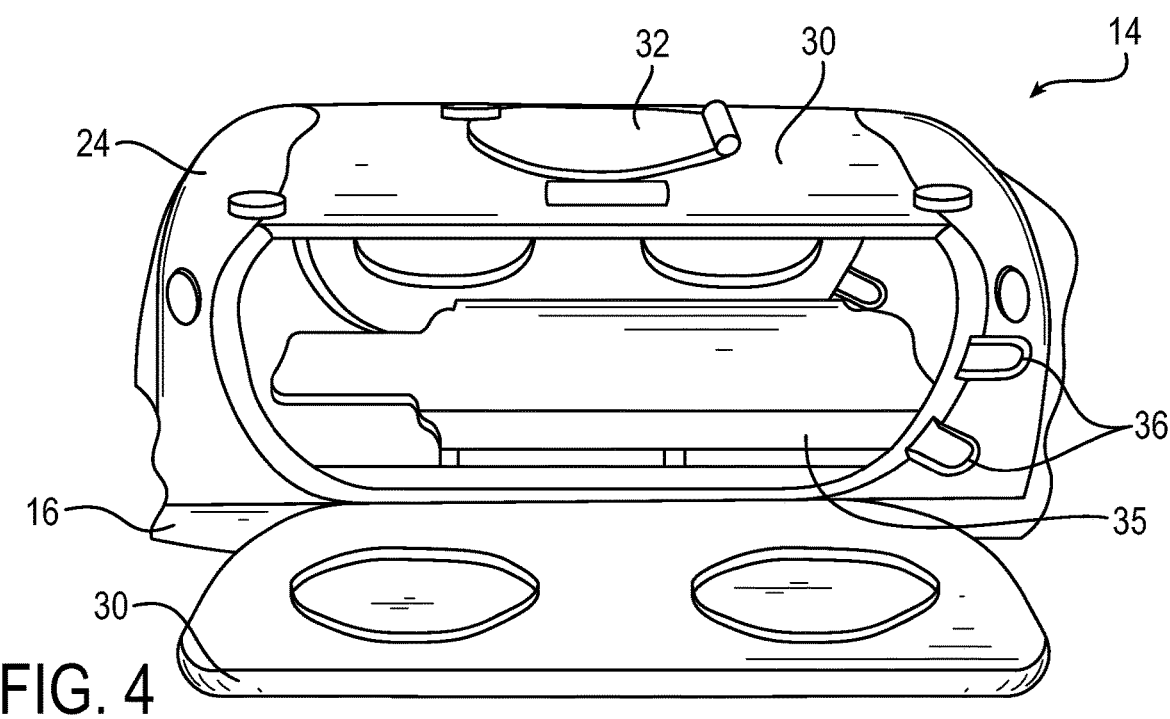
FIG. 4 is a detailed view of the isolette patient section of FIG. 3.

With reference to FIGS. 2, 3 and 4, an isolette 14 of the neonate imaging subsystem 12 can be formed as a portable, modular unit that, for example, weighs roughly 65 lbs. and is approximately 4 feet long. Assuming two caregivers lifting the isolette, this weight is far below the 50 lbs. per person limit for direct weight lifting according to OSHA standards for a hospital caregiver. The isolette 14 can include ergonomic handles 16 with wide spacing between grips for better balancing and ease of equipment handling by caregivers (e.g., a nurse and/or MR technician during staged transfers between a trolley 18 (FIG. 2) and MR patient table). The isolette 14 is designed to fit flat or curved MR patient tables. The isolette 14 can be powered via a connector 20 that couples power to a high power heater (not shown) and low level sensor cables (which may originate from a control unit).

The isolette 14 can include two sections, a patient section 24 and a heating section 26. The patient section 24 can include a transparent double walled housing 28 that enables complete view of the patient at all times. The patient section 24 can be configured to minimize heat transfer due to convection or radiation. The heating section 26 can receive filtered air, which is forced over a heater (not shown) and enters the patient section 24 on either side of the infant. A temperature regulator in accordance with the present disclosure, which may be implemented within a control unit, utilizes actual temperature feedback to maintain isolette air temperatures between, for example, 28 to 39° C. Regulation can be based on the air temperature measured in the patient section 24 and/or the air temperature measured in the heating section 26 in combination with the temperature of the ambient surrounding environment and/or or the skin temperature (skin temperature may be continuously monitored at the axilla (under the arm) or preferably the torso). Temperature sensors external to the isolette was well as within the patient section and heater section can be communicatively coupled to the control unit for use in regulating temperature in the patient section. The control unit may include a processor and memory that stores logic that causes the processor to carry out a method of regulating temperature in the isolette in accordance with the present disclosure.

The isolette 14 includes a special ambient mode where based on various parameters as discussed in more detail below, maximum power to the heater is limited and/or interrupted and only freshly filtered air is introduced in the patient section 24. To maintain appropriate temperatures as prescribed by a physician, air temperatures and patient skin temperature are continuously monitored during patient preparation in the intensive care unit, during transport between sections, and during the radiology exam.

The patient section 24 of the isolette 14 can include double-walled doors 30 for complete access on either sides in the case of emergency as well as portals (e.g., hand ports) 32 on all three sides for immediate patient access. The top portal allows administration of substances, such as medications, sugar drops, etc. Also, air pathways and tubes exiting patient airways can be adjusted via the top portal. Portals 32 are also provided at either end of the isolette 14 to enable life sustaining/monitoring lines to be connected to the infant at all times without compromising care and to enable RF coil connections to the MR scanner. An RF coil (not shown), which can be introduced or withdrawn through a door 33 superior to the patient, can slide under a cradle 35 without disturbing the patient inside the isolette 14.

Flaps 36 can be provided on rubber gaskets that seal the portals 32, the flaps 36 being designed to hold lines (not shown) extending out of the patient section 24 and connecting to the respective devices. Such flaps 36 enable a clutter-free area around the isolette 14. The flaps 36 can hold the lines during transport and minimize the possibility of such lines being pinched or caught during transport or movement of the isolette 14 and as the isolette 14 is removed from the trolley 18 and/or the MR patient table.

MR Compatible Trolley

Figure 5:
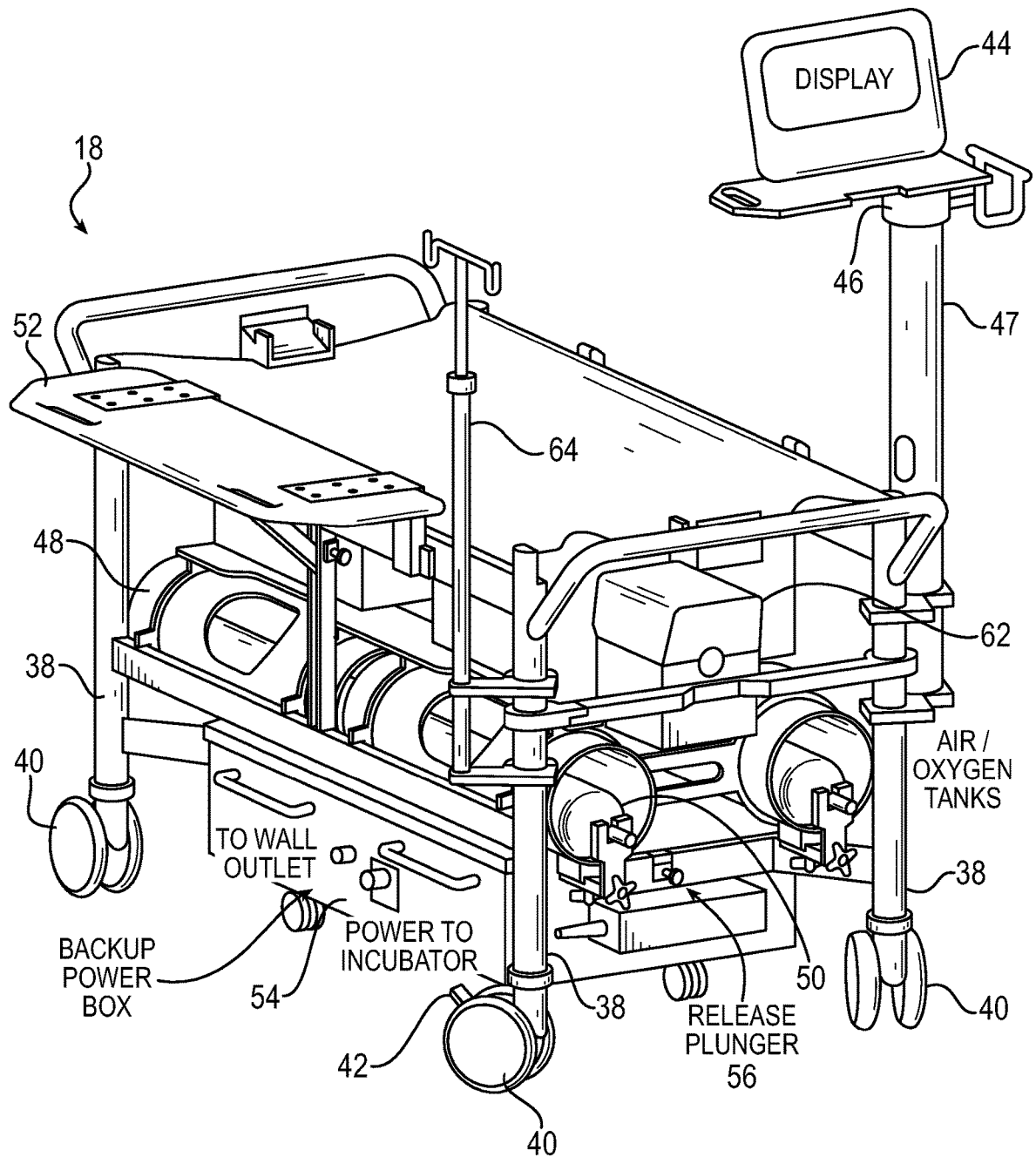
FIG. 5 is a perspective view of an MRI-compatible trolley transfer table that may be used to transport the isolette.

Referring to FIGS. 2 and 5, the exemplary trolley 18 is made of MR compatible material, such as aluminum, for example. The trolley 18, which is contoured to fit narrow hallways and elevator doors in the hospital, can include shock absorbers (not shown) atop the unit where the isolette 14 is placed. Shock absorbing struts 38 can be located on all four posts, which rest on freely moving rubber wheels 40. Directional locks (not shown) that aid transport by one caregiver can also be provided. Non-directional locks (or brakes) 42 that restrict trolley motion, for example during transfer of the isolette 14 to/from the MR patient table, during an emergency procedure performed outside of the routine area (e.g., in hallways, elevators, etc.) or during transport (e.g., in a vehicle) can be provided. Accordingly, the trolley 18 can provide shock-free transport of an infant inside the isolette 14 and is robust enough for routine use in a hospital environment (sharp 90 degree bends, wheel chair accessible incline/decline ramps, etc.).

A display/control unit 44 can be located at face height and affixed to a swivel base 46 via post 47 that is attached to the trolley 18. The swivel base 46 enables +/−120° rotation. A graphic user interface can be displayed on the display/control unit 44, and user interaction can be enhanced with audio and video information (e.g., alarms, etc.). Further, environment isolette control is possible via feedback from fiber-optic sensors located on the sub-system. This helps the isolette 14 adapt to the surrounding temperature without deviating from the stringent operation, performance and safety standards set for medical transport isolettes. Narrow and broad band filtering schemes over the nuclear magnetic resonance (NMR) spectrum, shielded coaxial cables, grounding considerations, etc. are included to reduce EMI/EMC radiation, eliminate undesired harmonics, and minimize risks of high voltage exposure, while maintaining leakage currents below the required IEC guidelines for safe operation of medical equipment.

The trolley 18 can include adjustable restraint mechanisms 48 to accommodate different size oxygen/air tanks 50, e.g., to hold them in place during transport. The trolley 18 can also be designed to accommodate monitoring equipment, infusion pumps, injectors and the like with an easy on/off mechanism (not shown) for enabling/disabling the respective components.

The trolley 18 includes a transfer table 52 that assists with transfer of the isolette 14 to and from the MR patient table. The transfer table 52 extends downward at right angles and locks in to place. In the extended position, the transfer table 52 is supported by the height adjustable MR patient table (not shown), which is designed to bear the weight of the isolette 14 and share the weight bearing between the trolley 18 and the MR patient table. Staged transfer, as opposed to a single transfer sideways swinging motion, is preferred by caregivers and poses less risk to hip twisting while transferring the isolette 14. Thus, operator safety is enhanced.

A battery power supply box 54 (FIG. 5), which may be on rollers, slides in and out of trolley guide rails and is held in place via a spring loaded plunger 56. This battery box can be slid out by simultaneously pulling the plunger and handle.

MR Compatible Ventilator

With reference to FIGS. 2 and 3, a MR compatible ventilator 58 with an in-built blender 59 can be used with the isolette 14. The ventilator 58 can be placed atop the isolette 14, over the heating section 26. A ventilator is typically used with patients who have a compromised respiratory system and may not be able to breathe on their own. A blender 59 is used in conjunction with the ventilator to provide a precise mixture of oxygen with air as prescribed by the physician. Input to the blender 59 comes from the oxygen/air tanks 50 whereas, the primary output of the blender 59 is provided to the ventilator 58. The inspiration/expiration rates that vary from patient to patient are set by controls on the ventilator 58, while the flow rate is controlled by the ventilator 58 based on the set rate. The ventilator 58 can be pneumatically driven and hence does not interfere with the performance of the isolette 14 or the MR system.

A backup mechanism can be installed on the ventilator 58 such that in the event the ventilator fails, the user has the option to connect a mechanical aspirator (e.g., a manually pumped balloon) to an auxiliary output of the blender 59 to support the infants breathing. Alternatively, the user also has the option to connect the oxygen/air lines directly to the ventilator 58 or to the infant in the event of blender failure. In all cases, appropriate flow rates are maintained and controlled by pressure reducers, flow tubes and the ventilator 58 to prevent excess flow to the infant. This is important, for example, in patients with encephalopathy in the first few weeks of life, where if excessive oxygen is passed to the patient damage to the eyes (hyperoxia) may occur, or if insufficient oxygen is passed to the infant damage to the brain (hypoxia) can occur. Hence the condition hypoxic-ischemic encephalopathy (HIE), severe HIE in some cases leads to cerebral palsy (CP).

MR Compatible Intravenous I/V Bags

A MR compatible IV pole 64 can be included with the trolley 18. Using MR compatible clips, the MR compatible IV pole 64 enables one or more IV bags to be held atop the trolley 18 close to the MR magnet.

MR Compatible Monitor

Vital signs monitoring is important for the thermoregulatory system compromised infant. Vital signs, such as ECG for measuring heart rate and shape, $SpO_2$ for measuring the patient's oxygen saturation in the blood, NIBP for non-invasively measuring blood pressure, end tidal $CO_2$, which measures the CO2 build up (an increase in $CO_2$ should cause for alarm, high levels of $CO_2$ is deleterious to the health of the subject); skin temperature which serves to monitor the overall status of the patient and its immunity to fight antibodies, etc., can be viewed on the MR compatible monitor/control unit 44. The MR compatible monitor/control unit 44, which does not produce artifacts during an MR scan, can be integral with the isolette 14 or may be a separate unit attached to the trolley 18 as shown in FIG. 5.

MR Compatible Fiber Optic Camera w/Remote Display

An MR compatible fiber optic camera can be used to monitor the infant at all times, especially when the subject is inside the MRI scanner. A remote display can be used inside or outside the MRI scan room for monitoring the infant. Again, care must be ensured that the fiber-optic camera and the display do not interfere with the performance of the isolette or the scanner.

Measures employed in U.S. patent application Ser. No. 10/723,325 filed Nov. 26, 2003 to Srinivasan with regard to the compatibility of the accessory to MR may be applied to the MR infusion pump, injector, ventilator, patient monitor, the display monitor and in general to all electronic items placed in or near the MR magnet.

Custom RF Coil

As noted above with respect to FIG. 2, an MR compatible RF coil may be inserted into and removed from the isolette 14 via door 33. Details of a custom isolette compatible RF coil can be found in U.S. Pat. Nos. 6,992,486 and 8,147,396 to Srinivasan, each of which is incorporated by reference in its entirety. Custom RF coils for imaging the brain, spine, heart, major organs and extremity generally fits $95^{th}$ percentile of the patient population. Anterior access to the patient is provided in the coil design, which also helps in the visual monitoring of the infant. The coil can be quickly placed in and out of the isolette 14 by opening the rear door 33 through which the coil 34 is introduced. The coil 34 can be held in place by sliding it under the isolette cradle 35 without disturbing the infant. The coil design incorporates the possibility of the coil being exposed to relatively higher temperatures (up to 39 deg C.), high levels of humidity (of up to 100% rH) and greater levels of oxygen (up to 100%). Thus the coil 34 is designed to withstand the harsh isolette environment without compromising the safety of the experiment and the SNR.

Temperature Control

Figure 6:
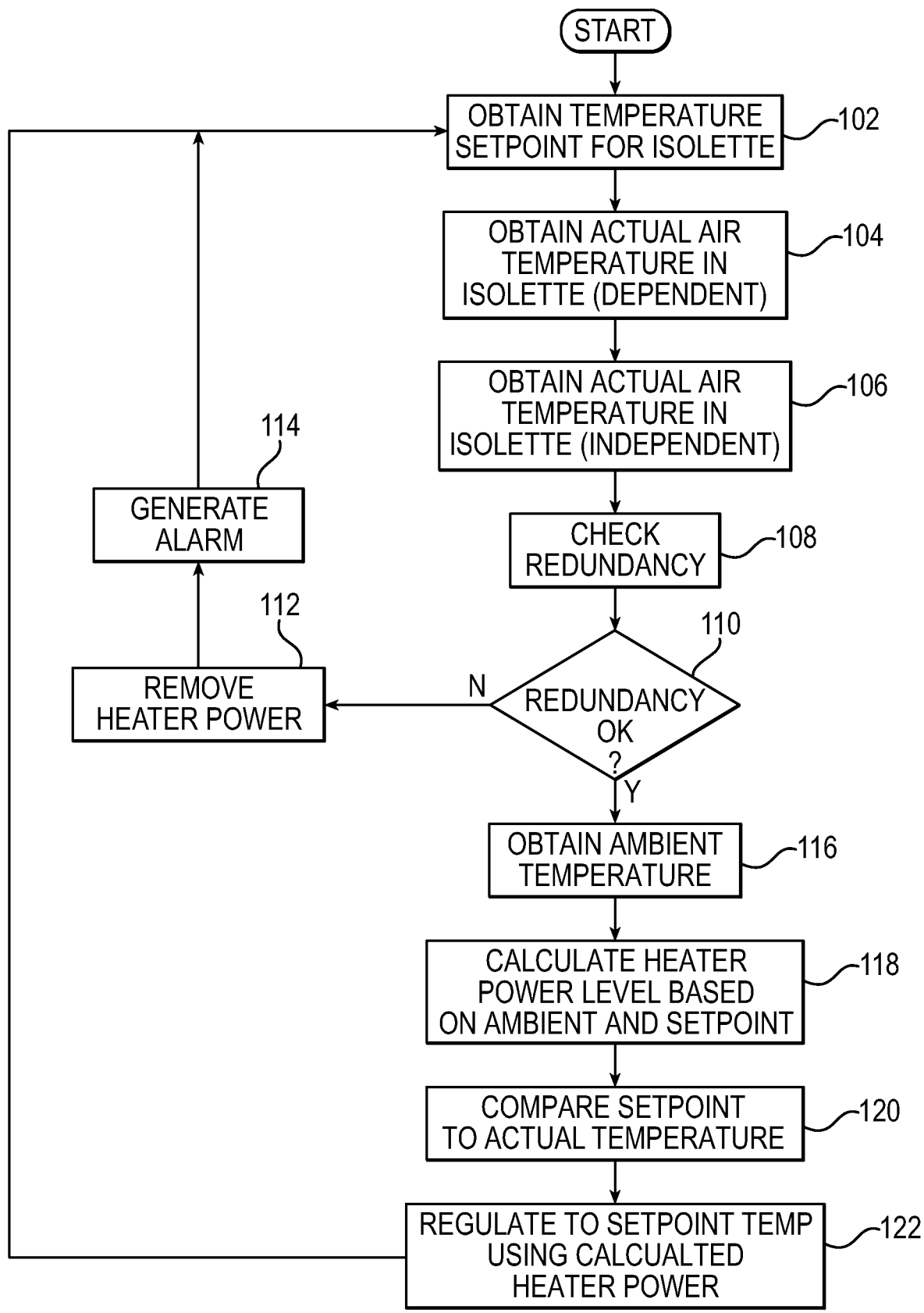
FIG. 6 is a flow chart illustrating an exemplary method for controlling temperature in an isolette in accordance with the present disclosure.

Referring now to FIG. 6, illustrated is a flow chart illustrating steps for an exemplary method for controlling temperature within an isolette 14 in accordance with the present disclosure. The flow chart includes a number of process blocks arranged in a particular order. As should be appreciated, many alternatives and equivalents to the illustrated steps may exist and such alternatives and equivalents are intended to fall within the scope of the claims appended hereto. Alternatives may involve carrying out additional steps or actions not specifically recited and/or shown, carrying out steps or actions in a different order from that recited and/or shown, and/or omitting recited and/or shown steps. Alternatives also include carrying out steps or actions concurrently or with partial concurrence.

Beginning at step 102, a temperature setpoint for the isolette 14 is obtained. Such temperature setpoint may be specified by a physician and entered, for example, via a user interface or the like. Next at steps 104 and 106 the actual air temperature within the isolette 14 is obtained. In accordance with a preferred embodiment, the actual air temperature is obtained using at least two temperature sensors, where a first temperature sensor may be used to regulate the temperature within the isolette 14 while a second temperature sensor may be used for redundancy purposes.

For example, at steps 108 and 110 a redundancy check can be performed where the temperature reading obtained from the first temperature sensor is compared to the temperature reading obtained from the second temperature sensor. If the temperature readings between the first and second sensors are not within the acceptable range or not within a prescribed tolerance value, the method moves to step 112 where power to the heater 26 is removed. For example, power may be provided to the heater 26 via a switching device. If the redundancy check fails, the control unit can command the switch to open, thereby removing power from the heater 26. Next at step 114 an alarm may be generated to notify a nurse or physician that there is a problem with one or both of the temperature sensors, and then the method moves back to step 102.

Moving back to step 110, if the redundancy check passes (e.g., the temperature reading of the first and second sensors are within a prescribed range and/or tolerance value of each other), the method moves to step 116 where the ambient temperature outside of the isolette 14 is obtained via a third temperature sensor. At step 118, the measured ambient temperature is used to calculate a power level for the heater. For example, the measured ambient temperature may be compared to a base-line ambient temperature. If the measured ambient temperature is greater than the base-line ambient temperature, then the maximum power supplied to the heater 26 may be limited (e.g., the maximum current provided to heating element can be limited to lower the maximum possible heat output by the heating element) as the warmer ambient requires less work from the heater 26. Conversely, if the actual ambient temperature is less than the base-line ambient temperature then the maximum power supplied to the heater 26 can be increased (e.g., the maximum current provided to the heating element can be increased to increase the maximum heat output by the heating element) as the colder ambient requires more work from the heater 26. An exemplary equation for determining the maximum power provided to the heater is provided in Equation 1, where Hp is the calculated maximum heater power, Tb is the base-line ambient temperature, Ta is the actual ambient temperature, and Pr is the regulated power of the heater.

$$Hp = Tb/Ta * Pr \qquad \text{Equation 1}$$

It is worth noting, other complex equations can be realized depending on the intended application.

Figure 7:
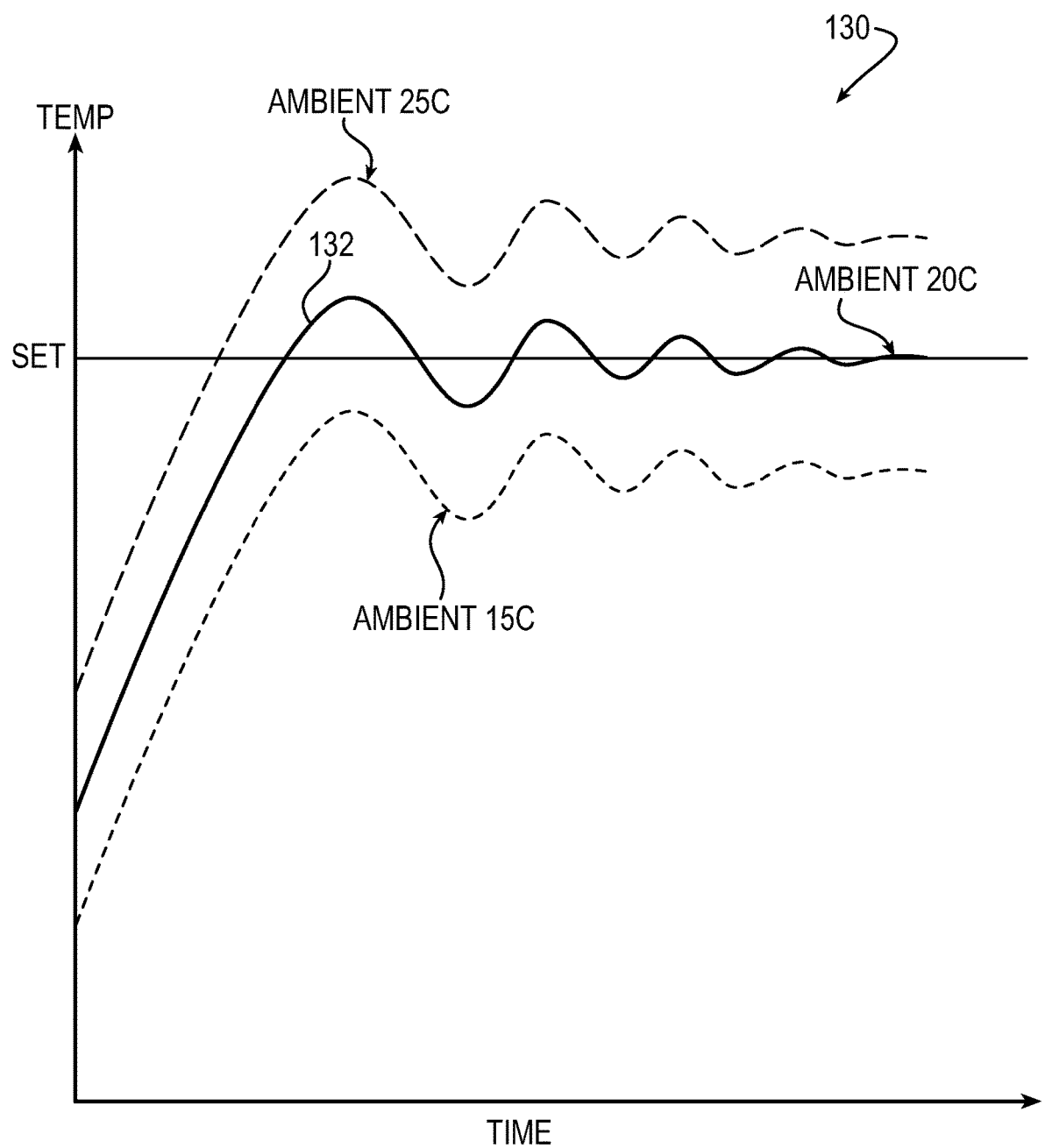
FIG. 7 is a graph showing temperature response within the isolette due to different ambient conditions.

With additional reference to FIG. 7, by regulating the maximum power provided to the heater 26 a heat-rise curve 130 can be made to coincide with that of a baseline value 132. Such maximum heater power regulation is beneficial to minimize the likelihood of overheating due to ambient environments having elevated temperatures, and to minimize the likelihood of insufficient heating in ambient environments with lower temperatures.

Next at step 120 the temperature setpoint as obtained at step 102 is compared to the measured temperature within the isolette 14 as obtained at step 104, and at step 122 the heater 26 is commanded to increase or decrease heat output so as to regulate the isolate temperature. Steps 120 and 122 may be implemented as a PID controller or the like that is executed by the control unit.

Accordingly, the regulation method regulates not only the maximum power supplied to the heater, but also the heat output provided by the heater. By regulating the maximum power supplied to the heater independent of a commanded heat output from the heater, temperature regulation within the isolette 14 is improved, particularly when the isolette 14 is transferred from one ambient environment to another. Such regulation is also beneficial to maintain adequate heating power (and thus prevent over heating) when the doors 30 or 33 and/or portals 32 are left open for extended periods of time.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

What is claimed is:

1. A method of controlling a temperature within an isolette, the isolette including a patient section for housing an infant and for receiving heated air from a heater, the method comprising:
   obtaining a temperature of ambient air external to the isolette;
   obtaining a base-line ambient air temperature;
   calculating a maximum heater power level based on a relationship between the base-line ambient air temperature and the actual ambient air temperature.

2. The method according to claim 1, wherein calculating a maximum heater power includes using a ratio of the base-line ambient temperature relative to the actual ambient temperature.

3. The method according to claim 1, wherein calculating includes calculating the maximum heater power using the formula $Hp=Tb/Ta*Pr$, where Hp is the calculated maximum heater power, Tb is the base-line ambient temperature, Ta is the actual ambient temperature, and Pr is the regulated power of the heater.

4. The method according to claim 1, further comprising:
   obtaining a temperature setpoint for the patient section;
   obtaining an actual temperature of the patient section; and
   regulating the actual temperature of the patient section by controlling the heater based on a relationship between the patient section temperature setpoint and the patient section actual temperature.

5. The method according to claim 4, wherein regulating the actual temperature includes using a PID controller to control an amount of heat supplied by the heater.

6. The method according to claim 1, wherein obtaining an actual temperature of the patient section includes:
   using a first temperature sensor to obtain a first temperature of the patient section;
   using a second temperature sensor to obtain a second temperature of the patient section; and
   removing power from the heater when a deviation between the first temperature and the second temperature exceeds a prescribed value.

7. The method according to claim 6, further comprising generating a warning when the deviation between the first temperature and the second temperature exceeds the prescribed value.

8. An isolette, comprising:
   a patient section for housing an infant;
   a heater for providing heat to the patient section; and
   a controller operatively coupled to the heater, the controller including
      logic configured to obtain a temperature of ambient air external to the isolette;
      logic configured to obtain a base-line ambient air temperature;
      logic configured to calculate a maximum heater power level based on a relationship between the base-line ambient air temperature and the actual ambient air temperature.

9. The isolette according to claim 8, wherein the logic configured to calculate a maximum heater power includes logic configured to use a ratio of the base-line ambient temperature relative to the actual ambient temperature to perform the calculation.

10. The isolette according to claim 8, wherein the logic configured to calculate includes logic configured to calculate the maximum heater power using the formula $Hp=Tb/Ta*Pr$, where Hp is the calculated maximum heater power, Tb is the base-line ambient temperature, Ta is the actual ambient temperature, and Pr is the regulated power of the heater.

11. The isolette according to claim 8, further comprising:
   logic configured to obtain a temperature setpoint for the patient section;
   logic configured to obtain an actual temperature of the patient section; and
   logic configured to regulate the actual temperature of the patient section by controlling the heater based on a relationship between the patient section temperature setpoint and the patient section actual temperature.

12. The isolette according to claim 11, wherein the logic configured to regulate the actual temperature includes logic configured to use a PID controller to control an amount of heat supplied by the heater.

13. The isolette according to claim 8, wherein the logic configured to obtain an actual temperature of the patient section includes:
   logic configured to use a first temperature sensor to obtain a first temperature of the patient section;
   logic configured to use a second temperature sensor to obtain a second temperature of the patient section; and logic configured to remove power from the heater when a deviation between the first temperature and the second temperature exceeds a prescribed value.

14. The isolette according to claim 13, further comprising logic configured to generate a warning when the deviation between the first temperature and the second temperature exceeds the prescribed value.

15. A controller for regulating a temperature within a patient section of an isolette, the controller comprising:
- a processor and memory; and
- logic stored in the memory and executable by the processor, wherein when executed by the processor the logic causes the processor to perform the method according to claim 1.

16. The controller according to claim 15, further comprising logic configured to provide regulated heater power to a heater, wherein the regulated heater power is less than the maximum heater power level.

17. The isolette according to claim 8, wherein the controller includes logic configured to provide regulated heater power to the heater, wherein the regulated heater power is less than the maximum heater power level.

18. The method according to claim 1, further comprising providing regulated heater power to a heater, wherein the regulated heater power is less than the maximum heater power level.

* * * * *

UNITED STATES PATENT AND TRADEMARK OFFICE
CERTIFICATE OF CORRECTION

PATENT NO. : 10,543,141 B2
APPLICATION NO. : 15/560333
DATED : January 28, 2020
INVENTOR(S) : Ravi Srinivasan Page 1 of 1

It is certified that error appears in the above-identified patent and that said Letters Patent is hereby corrected as shown below:

In the Specification

In Column 1, under RELATED APPLICATION DATA, the filing date of the priority PCT application identified as "Mar. 23, 2017" should read --Mar. 23, 2015--

Signed and Sealed this
Seventh Day of April, 2020

Andrei Iancu
*Director of the United States Patent and Trademark Office*